United States Patent
Rompen et al.

(10) Patent No.: US 10,251,974 B2
(45) Date of Patent: Apr. 9, 2019

(54) BONE REGENERATION MATERIAL AND MANUFACTURE METHOD THEREOF

(71) Applicant: WISHBONE, Flemalle (BE)

(72) Inventors: Eric Rompen, Embourg (BE); France Lambert, Liège (BE); Geoffrey Lecloux, Chaudfontaine (BE); Philippe Moniotte, Héron (BE)

(73) Assignee: Wishbone, Flemalle (BE)

( * ) Notice: Subject to any disclaimer, the term of this patent is extended or adjusted under 35 U.S.C. 154(b) by 0 days.

(21) Appl. No.: 15/026,217

(22) PCT Filed: Oct. 2, 2014

(86) PCT No.: PCT/EP2014/071157
§ 371 (c)(1),
(2) Date: Mar. 30, 2016

(87) PCT Pub. No.: WO2015/049336
PCT Pub. Date: Apr. 9, 2015

(65) Prior Publication Data
US 2016/0235885 A1 Aug. 18, 2016

(30) Foreign Application Priority Data

Oct. 3, 2013 (BE) .................................. 2013/0660

(51) Int. Cl.
*A61L 27/12* (2006.01)
*A61L 27/36* (2006.01)
*A61L 27/54* (2006.01)
*A61L 27/56* (2006.01)

(52) U.S. Cl.
CPC ............. *A61L 27/12* (2013.01); *A61L 27/365* (2013.01); *A61L 27/3608* (2013.01); *A61L 27/3687* (2013.01); *A61L 27/3691* (2013.01); *A61L 27/54* (2013.01); *A61L 27/56* (2013.01); *A61L 2430/02* (2013.01)

(58) Field of Classification Search
CPC .. A61L 2430/02; A61L 27/12; A61L 27/3608; A61L 27/365; A61L 27/3687; A61L 27/3691; A61L 27/54; A61L 27/56
See application file for complete search history.

(56) References Cited

U.S. PATENT DOCUMENTS

| | | | |
|---|---|---|---|
| 5,417,975 A * | 5/1995 | Lussi | .................. A61L 27/3608 424/423 |
| 2003/0014124 A1 * | 1/2003 | Wolfinbarger, Jr. | ........................ A61L 27/3608 623/23.63 |

FOREIGN PATENT DOCUMENTS

WO 96/12509 A1 5/1996

OTHER PUBLICATIONS

International Search Report dated Oct. 31, 2014, issued in corresponding International Application No. PCT/EP2014/071157, filed Oct. 2, 2014, 4 pages.

* cited by examiner

*Primary Examiner* — Michael B. Pallay
(74) *Attorney, Agent, or Firm* — Christensen O'Connor Johnson Kindness PLLC

(57) ABSTRACT

Described herein is a method that comprises: —placing a bone material, containing hydroxyapatite and organic substances, in contact with an extraction liquid that gives rise to a first liquid phase, containing the organic substances and possibly impurities extracted from the bone material, and a second solid hydroxyapatite phase, containing the hydroxyapatite; and —separating the liquid phase and the solid hydroxyapatite phase. The extraction liquid is an aqueous extraction solution brought to a temperature between 150° C. and 300° C. and a pressure between 150 kPa and 350 kPa.

10 Claims, 8 Drawing Sheets

BONE REGENERATION MATERIAL AND MANUFACTURE METHOD THEREOF

TECHNICAL FIELD

Embodiments of the present disclosure relate to a method for manufacturing bone regeneration material containing hydroxyapatite.

This type of bone regeneration material is used in particular for the treatment of bone deterioration in different fields of reparative or cosmetic surgery.

Hydroxyapatite is a calcium phosphate having osteoconductive properties and forms the main mineral component of bone; use thereof is therefore fully suitable for bone reconstructive or reparative surgery.

It is within this setting that numerous hydroxyapatite-containing materials are currently used for implants and in particular dental implants to stimulate bone reconstruction at defective or deteriorated bone sites.

These materials include artificial materials containing hydroxyapatite prepared via synthesis from phosphoric acid and calcium salts either using a direct precipitation process or process of sol-gel type.

However, the aforementioned synthesis methods do not allow a bone regeneration material to be obtained in which hydroxyapatite has a porous, spatial structure similar to the structure found in a bone matrix in the natural state.

This accounts for the current increasing interest in the use of hydroxyapatite of natural origin having the advantage of exhibiting identical crystalline structure and morphology to those of a bone material in the natural state.

In particular the use natural hydroxyapatite derived from bone samples, once cleaned of their organic substances comprising at least one component from the group formed by proteins such as prions, peptides and lipids, allows a matrix to be obtained that better lends itself to bone regeneration than its artificial analogue.

It is imperative that the bone regeneration material, in the implanted state for example, should be cleaned of any traces of organic substances so that after implantation it is well integrated into the body, is biocompatible and interacts with the biological environment in which it is placed via osteoconduction.

Within this context the present disclosure concerns a method to manufacture a bone regeneration material, comprising:
  contacting a bone material containing hydroxyapatite and organic substances with an extraction liquid giving rise to a liquid phase containing the organic substances and optionally impurities extracted from the bone material, and to a solid hydroxyapatite phase containing the hydroxyapatite, and
  separating the liquid phase from the solid hydroxyapatite phase.

BACKGROUND

This type of process is known for example from documents U.S. Pat. No. 5,417,975 and WO96/12509. More specifically, document U.S. Pat. No. 5,417,975 discloses the preparation of well-known bone regeneration material of natural origin, Bio-Oss®, and document WO96/12509 discloses the preparation of osteoconductive material.

Aside from the improved osteoconductive properties of natural bone regeneration material, the production thereof also allows recovery of butcher and slaughterhouse organic waste which forms a low-cost source having abundant bone material.

In the process of U.S. Pat. No. 5,417,975 the bone material is first degreased and then placed in a heated aqueous solution of primary amines or ammonia, preferably to a temperature between 80 and 200° C., wherein the organic substances are degraded and solubilized for final extraction by successive rinsing in demineralized water preferably heated to a temperature of between 20 and 60° C. at a water-flow rate advantageously of at least 10 cm per hour.

Degreasing is obtained by immersing the bone material in an organic solvent such as toluene or methylcyclohexane heated under reflux at a temperature of between 80 and 120° C.

According to U.S. Pat. No. 5,417,975 the contacting time between the bone material and the heated aqueous solution is dependent on the particle size of the material, on the reactivity of primary amines or ammonia solution and on the temperature to which this aqueous solution is heated. In general, this time is between 2 and 200 hours. For example, a bone material sample 1 cm in diameter treated with an aqueous ethylene diamine solution at 118° C. requires a treatment time of at least 50 hours to obtain satisfactory degradation of organic substances so that after rinsing their remaining content is lower than 150 ppm.

The bone material thus treated is then air dried at temperatures between 250° C. and 600° C. until the weight of the material stabilizes at a constant value. To obtain high purity bone regeneration material i.e. in which the organic substance content is lower than 150 ppm, the rinsing step with demineralized water must be performed continuously over a period ranging from 5 to 25 days.

Unfortunately the process suffers from several limitations. First it entails treatment using organic solvents the residues of which after treatment cannot be recycled and must be treated. Next this process involves treatment in an amine bath at 60° C. for more than 50 hours followed by rinsing in continuously flowing demineralized water over a period of at least 5 days. Clearly the lengthy time of the process (at least 5 days), moreover involving use of polluting organic products which must be treated, means that the process on industrial scale is costly and difficult to amortize.

SUMMARY

It is the objective of the disclosure to overcome the disadvantages of the state of the art by providing a method allowing faster manufacture of bone regeneration material free of any trace of undesirable organic substances that is simple to implement, the steps thereof having limited negative impact on the environment, and the byproducts of manufacture being easy to treat.

In addition it is the objective of the disclosure to propose a method for manufacturing a bone regeneration material in which all the steps can be performed on industrial scale continuously or semi-continuously in a single reactor. This industrial applicability is easy to obtain since the method of the disclosure is particularly efficient in terms of yield, in terms of energy consumption and only uses relatively low-cost reagents such as water and sodium hydroxide, additionally making available a "green" method, i.e., an environmentally-friendly method. In practice, the method must allow the manufacture of bone regeneration material obtained using the method of the disclosure in which the organic substance content is lower than 150 ppm.

Advantageously, the method must allow the manufacture of bone regeneration material containing proteins in a content lower than 130 ppm and be completely free of intact proteins or peptides, prions in particular.

To solve this problem the disclosure provides for a method such as first set out above characterized in that the extraction liquid is an aqueous extraction liquid brought to a temperature of between 150° C. and 300° C. at a pressure of between 1500 kPa and 3500 kPa, and in that the separated solid hydroxyapatite phase forms the bone regeneration material.

It has surprisingly been observed that the contacting of the bone material with the aqueous extraction liquid under so-called "intensified" conditions i.e. at a temperature between 150° C. and 300° C. and pressure between 1500 kPa and 3500 kPa allows the production of a solid hydroxyapatite phase exclusively containing hydroxyapatite forming the bone material, via extraction in the liquid phase of all the undesirable organic substances and other undesirable impurities which, if present in the solid phase, would compromise the biocompatibility of the hydroxyapatite and would increase rejection possibilities when inserted as bone implant. The characteristics of the water under intensified conditions are such that it acts both as solvent and reagent. The high temperature, i.e., between 150° C. and 300° C., used in the method has the effect of increasing dissociation of the water (and hence its reactivity), of accelerating every reaction in particular hydrolysis and of notably decreasing the viscosity of the solvent.

This last property being advantageous when treating an insoluble porous solid with a liquid reagent since the rate of diffusion of the liquid in the solid matrix determines efficacy and rate of chemical exchanges.

Within this fully unexpected context, it has been shown as part of this disclosure that the extraction and rinsing steps conducted under the temperature and pressure conditions of the disclosure only require a time in the order of 2 to 5 hours, contrary to the state of the art and in particular to document U.S. Pat. No. 5,417,975 in which this time is almost 50 hours, i.e., ten times higher. More specifically, according to the disclosure the extraction step itself is shorter than 1 hour which strongly limits energy consumption and makes the method of the disclosure all the more efficient and industrially applicable.

In addition, these conditions of temperature and pressure allow solubilization of organic compounds known to be water-insoluble under normal conditions of temperature and pressure. Also hydroxyapatite remains insoluble in the aqueous phase under these intensified conditions.

Optionally, prior to the drying step the first contacting step and the separation step are repeated several successive times.

Advantageously the method of the disclosure further comprises an additional drying step of the solid hydroxyapatite phase to obtain a dry solid hydroxyapatite phase.

Advantageously, the weight of the solid hydroxyapatite phase corresponds to a fraction of between 55 and 65%, preferably between 57 and 62% of the weight of the bone material, before it is treated using the method of the disclosure.

Preferably, the contacting of the bone material with the aqueous extraction solution is performed at a temperature between 220 and 250° C., advantageously lower than 240° C.

It has effectively been observed as part of this disclosure that the method reaches optimum efficacy at these temperatures, i.e. the method allows the manufacture of bone regeneration material in which the protein content is strictly lower than 130 ppm, higher temperatures leading to excessively fast decomposition of the proteins contained in the organic substances and their initial hydrolysis residues, i.e., promoting the formation in the hydroxyapatite phase of insoluble solid organic residues which cannot be extracted with the extraction liquid and whose presence may compromise the biocompatibility of the regeneration material.

Alternatively, the contacting of the bone material with the aqueous extraction solution is conducted at a pressure between 2500 kPa and 3000 kPa.

Advantageously, the aqueous extraction solution is water or a concentrated aqueous solution with basic pH e.g. formed from solubilization in water of a strong base preferably an alkaline hydroxide at a concentration of between 0.5 and 1 N, preferably between 0.6 and 0.9 N.

It has also been observed that at basic pH the extraction of organic substances, such as fatty acid residues generally scarcely soluble in water, is improved.

In addition, at a pH higher than 7 the solubility of hydroxyapatite remains very low. Therefore by performing the extraction step at basic pH, the insolubility of hydroxyapatite in the extraction liquid can be ensured.

In one particular embodiment of the method of the disclosure, the drying step is an oven drying step in dry heat at a temperature between 100° C. and 300° C., preferably at 120° C.

Preferably, after the first separation step and before the drying step of the solid hydroxyapatite phase, the method of the disclosure comprises a second contacting step of the solid hydroxyapatite phase with a dilute aqueous solution at basic pH at a temperature of between 150° C. and 300° C., preferably at 150° C. and at a pressure of between 99 kPa and 1000 kPa, preferably 500 kPa, the second contacting step being followed by a second separation step between a second liquid phase and second solid phase and subsequent drying.

Advantageously the dilute aqueous phase at basic pH is formed by solubilizing a strong base in water, preferably an alkaline hydroxide at a concentration between 0.05 and 0.4 N, preferably between 0.1 and 0.3 N.

Optionally, the solid hydroxyapatite phase is previously rinsed with water before being dried.

In one preferred embodiment the method of the disclosure is characterized in that prior to the first contacting step with the extraction liquid it comprises a degreasing and defleshing step of the bone material.

Preferably this degreasing and defleshing step is performed by contacting the bone material with an aqueous solution preferably at basic pH at a temperature of 100° C. or higher, preferably between 100 and 200° C.

Preferably the degreasing and defleshing step is followed by a step to scrape off residues of flesh, marrow and cartilage from the bone material.

Advantageously the method of the disclosure, after the drying step, comprises a sterilization step of the dry solid hydroxyapatite phase.

In one embodiment, the sterilization step is performed for example by heating the dry hydroxyapatite phase to 120° C. for 14 hours in an airtight fluoropolymer bag.

Preferably, the drying temperature is between 100° C. and 300° C. for a period of between 5 and 20 hours, preferably between 10 and 15 hours.

Preferably the bone material is of natural animal origin, e.g., from mammalian or oviparous animals and may be of bovine, ovine, equine or porcine origin and similar, in particular extracted from the epiphysis or metaphysis of these animals.

In general the bone material is derived from butchers' waste which means that the method of the disclosure has the advantage of recovering this abundantly available waste.

Other embodiments of the composition of the disclosure are given in the appended claims.

Embodiments of the present disclosure are also directed towards a bone regeneration material directly obtained using the method of the disclosure, comprising a solid hydroxyapatite phase obtained from a bone material of natural origin and having identical crystalline structure and morphology to those of the bone material.

Advantageously the solid phase solely comprises hydroxyapatite obtained from bone material of natural origin.

Preferably the bone material is derived from bovine or calf epiphyses or metaphyses.

In one particular embodiment, the bone regeneration material comprises organic substances in a content less than 150 ppm, the organic substances containing proteins in a content lower than 130 ppm.

Advantageously the material is intended to be used as implant or prosthesis for bone formation, bone regeneration or bone repair at a defective site in a mammalian, preferably a human.

It has additionally been shown according to the present disclosure that the bone regeneration material has a crystalline structure and morphology similar to those of Bio-Oss®.

Therefore, just like Bio-Oss®, the regeneration material obtained using the method of the disclosure is a macroporous material having pores of diameter 50 μm or larger, preferably between 50 and 100 μm.

Other embodiments of the method of the disclosure are given in the appended claims.

The present disclosure also relates to a medical device containing a bone regeneration material of the disclosure.

Other embodiments of the medical device of the disclosure are given in the appended claims.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

DETAILED DESCRIPTION

The detailed description set forth below in connection with the appended drawings is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

In the following examples the bone material was previously degreased and defleshed by extended boiling in water following by scraping to remove residues of flesh, marrow and cartilage.

Example 1

50 g of degreased, defleshed bone material containing hydroxyapatite, 400 ml of demineralized water and 10 g of a strong base (NaOH) were mixed in an autoclave reactor without agitator brought to a temperature of 220° C.±2° C. via external heating using an electric jacket. The pressure in the reactor was brought to 2500 kPa. These conditions of temperature and pressure were held for a time of one hour.

The reactor was cooled down to ambient temperature and depressurized to atmospheric pressure, a homogenous liquid phase was removed from the reactor by decanting so that only the solid phase remained in the reactor to which was added 5 g NaOH in solution in 400 ml of demineralized water.

The autoclave reactor was then brought to a temperature of 150° C. under atmospheric pressure (about 100 kPa) for a time of one hour.

The reactor was again cooled down to ambient temperature, the reactor content decanted and the solid phase, a solid hydroxyapatite phase, was rinsed with demineralized water and oven dried at a temperature of 120° C. until stabilization of its weight at around a stationary value.

Figure 1:
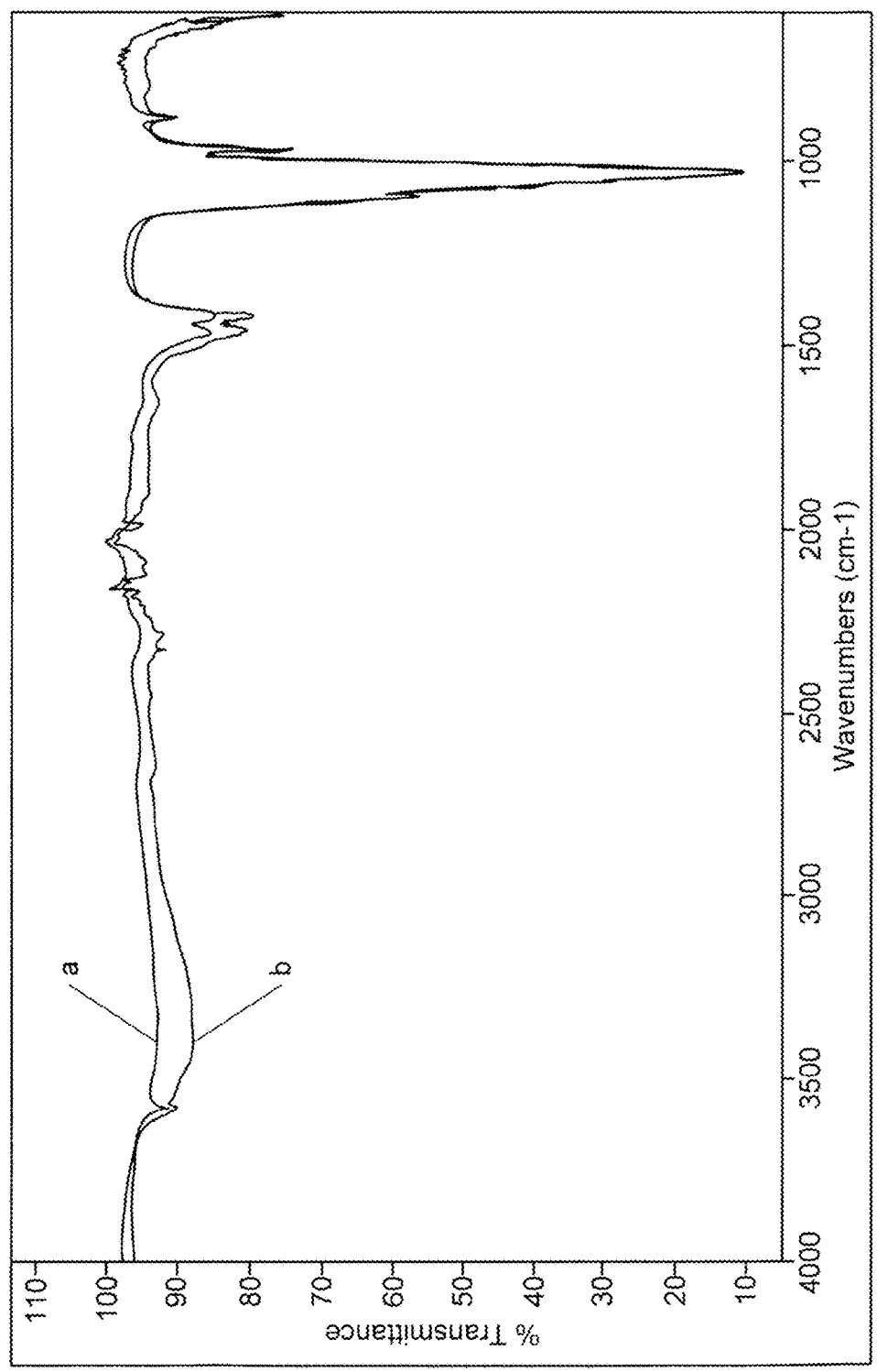
FIG. 1 illustrates superimposed infrared spectra (IR) of the regeneration material (a) obtained using the method of the disclosure and of Bio-Oss® (b).

The solid hydroxyapatite phase formed the bone regeneration material for which the IR spectrum is given in FIG. 1 and compared with that of Bio-Oss®. The IR spectra are identical indicating that the bone regeneration material obtained with the method of the disclosure is identical to Bio-Oss®.

Figure 2:
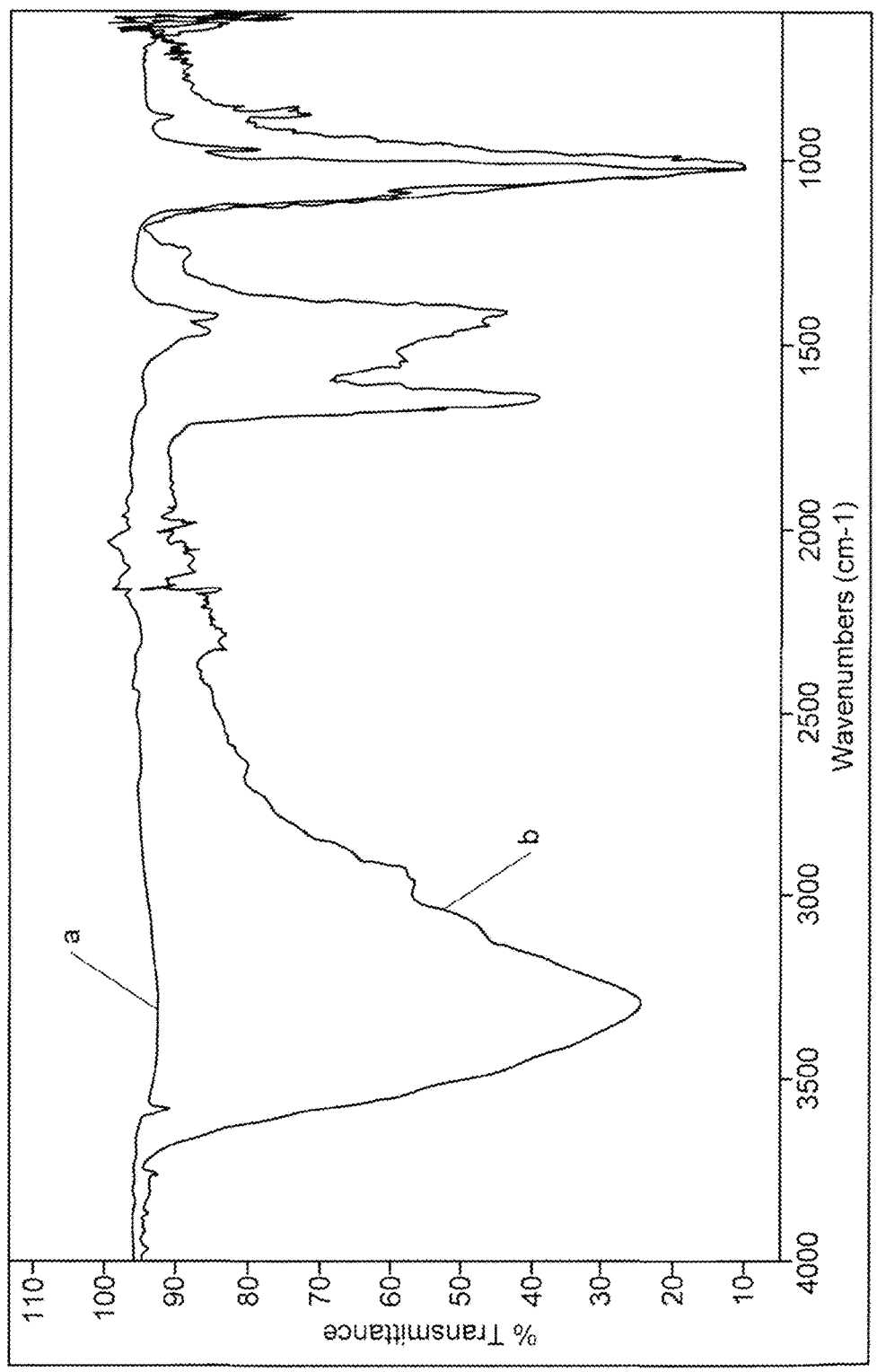
FIG. 2 illustrates superimposed IR spectra of the regeneration material (a) obtained using the method of the disclosure and of bone material (b) before treatment with the method of the disclosure.

FIG. 2 illustrates the superimposition of the IR spectrum of the regeneration material (a) obtained with the disclosure and the IR spectrum of the bone material (b) before treatment with the method of the disclosure.

This superimposition shows the contribution of proteins in the bone material towards the composition of the IR spectrum of the regeneration material of the disclosure. This contribution is chiefly characterized by very intense absorption bands between 3500 and 3000 cm−1 and between 1750 and 1500 cm−1 which are no longer observed in the regeneration material obtained with the method of the disclosure.

Figure 3:
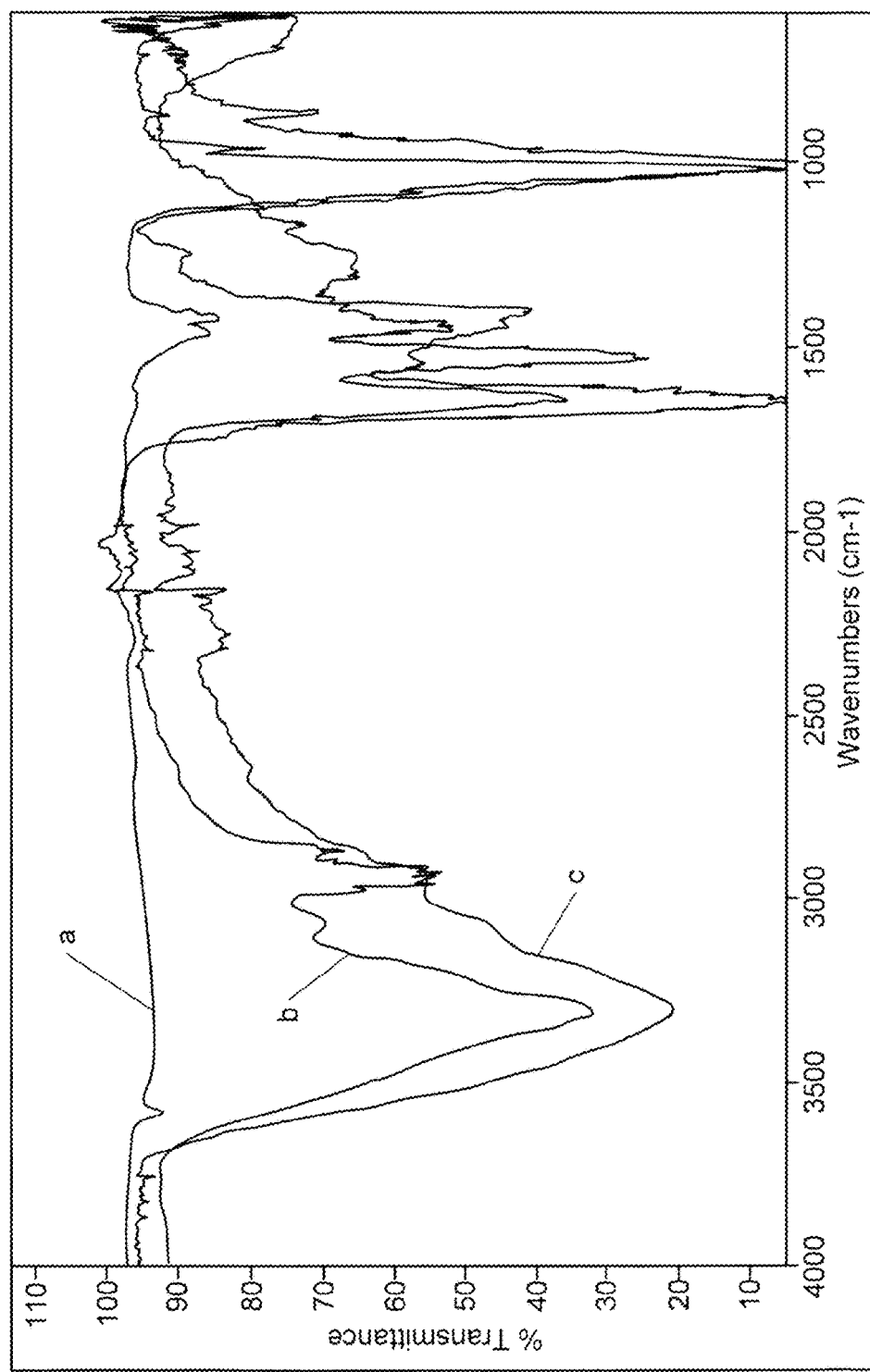
FIG. 3 illustrates superimposed IR spectra of regeneration material (a) obtained using the method of the disclosure, of bone material (b) before treatment with the method of the disclosure and of a reference protein: zein (c).

FIG. 3 illustrates the comparison between the IR spectra of the defleshed degreased bone material and of a reference protein: zein. The correspondence between the specific peaks in regions of the electromagnetic spectrum positioned between 3500 and 3000 cm−1 and between 1750 and 1500 cm−1 confirms the almost exclusive presence of proteins in the bone material after degreasing and defleshing thereof.

Figure 4:
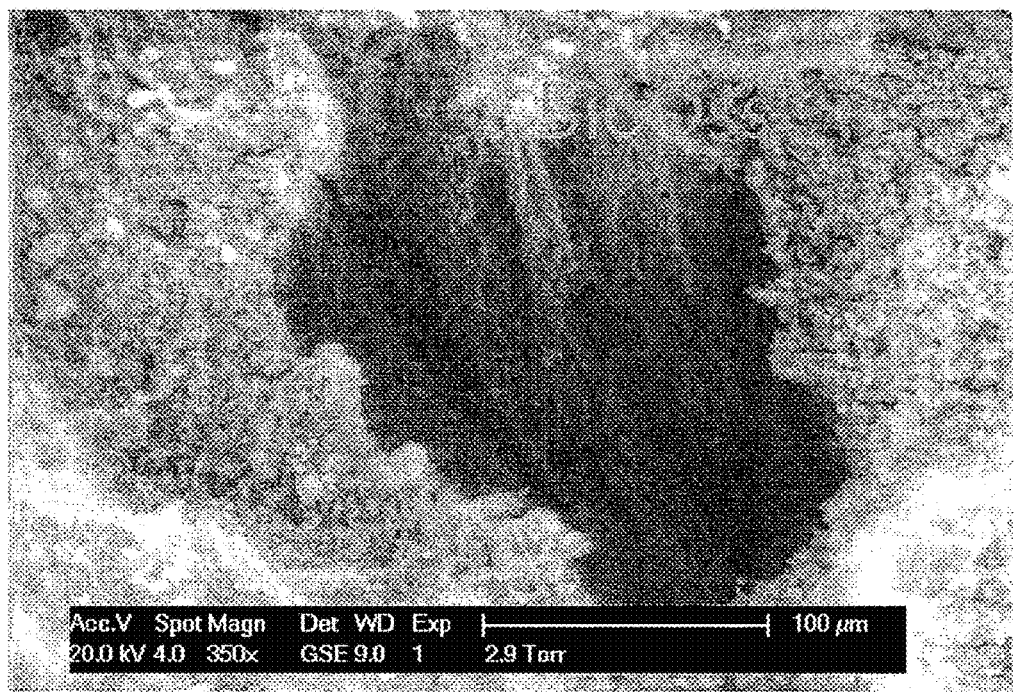
FIG. 4 gives an image obtained by scanning electron microscopy (SEM) of the structure of Bio-Oss® on a scale ranging from 0 to 100 μm.

FIG. 4 is a SEM image of the structure of Bio-Oss® confirming the macroporous structure thereof. On reading FIG. 4 it can clearly be seen that this material has a structure comprising two types of pores: pores of diameter about 50 μm corresponding to extraction of the proteins and pores of diameter about 100 μm inherent in the structure of the bone material.

Figure 5:
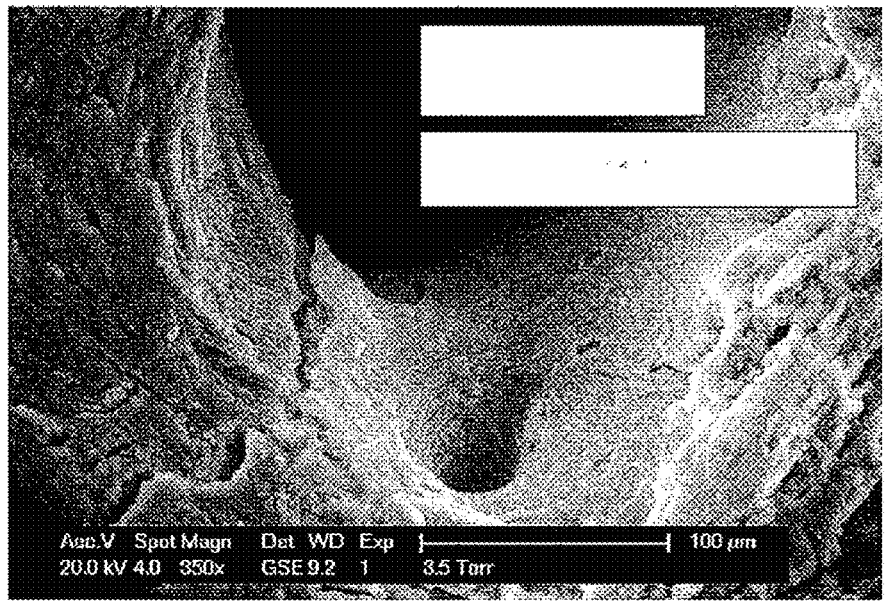
FIG. 5 gives two SEM images taken on a scale ranging from 0 to 50 μm and a scale ranging from 0 to 100 μm of the bone regeneration material obtained with the method of the disclosure from bovine epiphysis.
Figure 5:
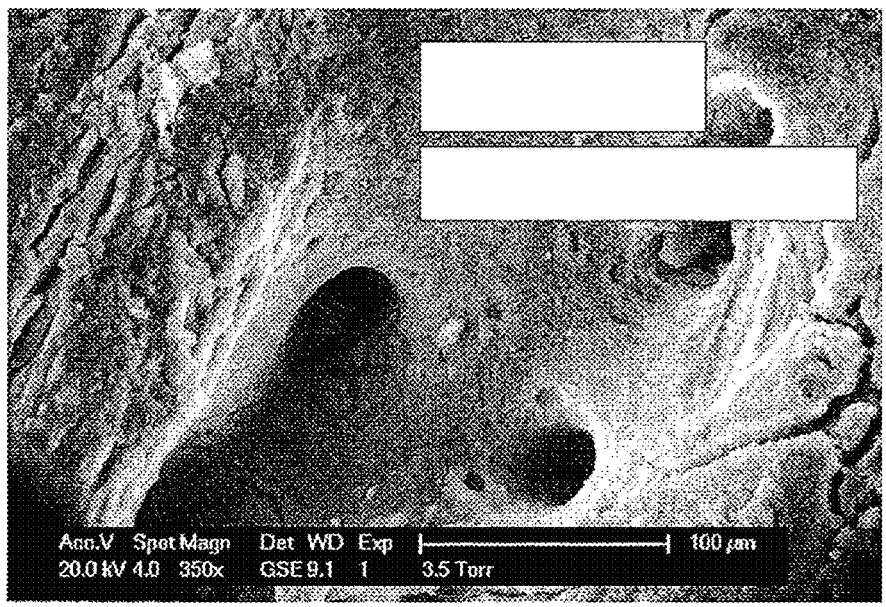
Figure 6:
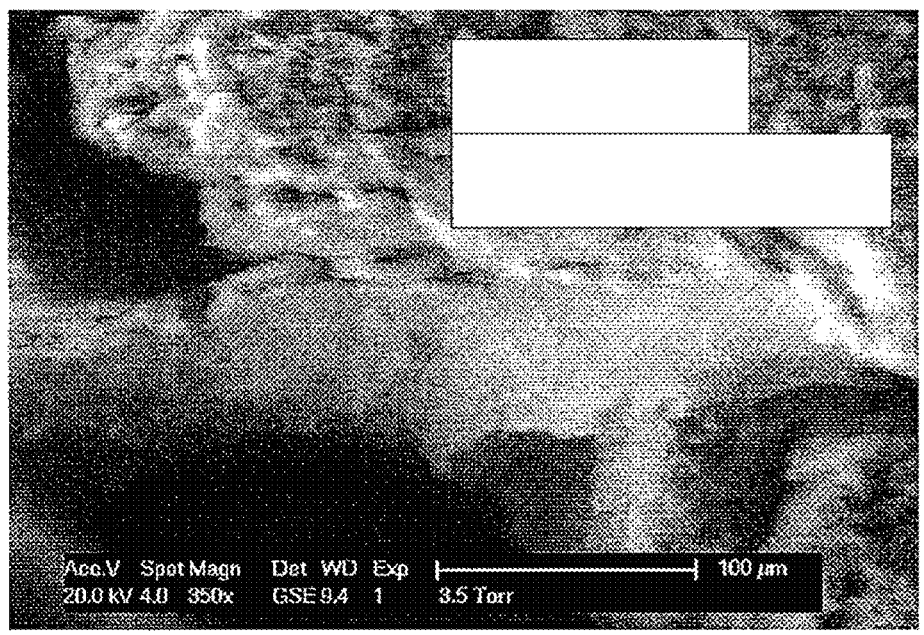
FIG. 6 gives two SEM images taken on a scale ranging from 0 to 100 μm of the bone regeneration material obtained using the method of the disclosure from calf metaphysis.
Figure 6:
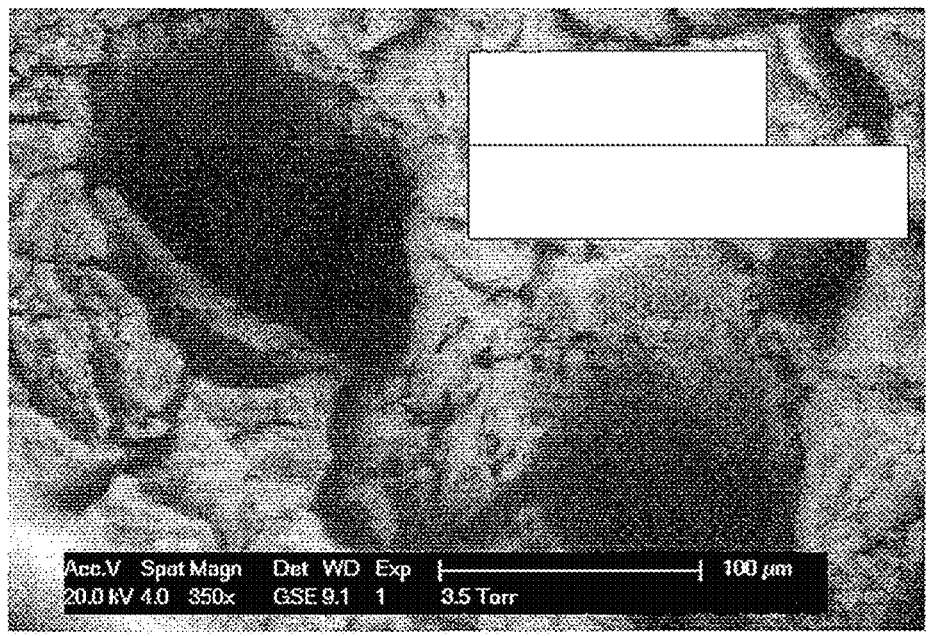
Figure 7:
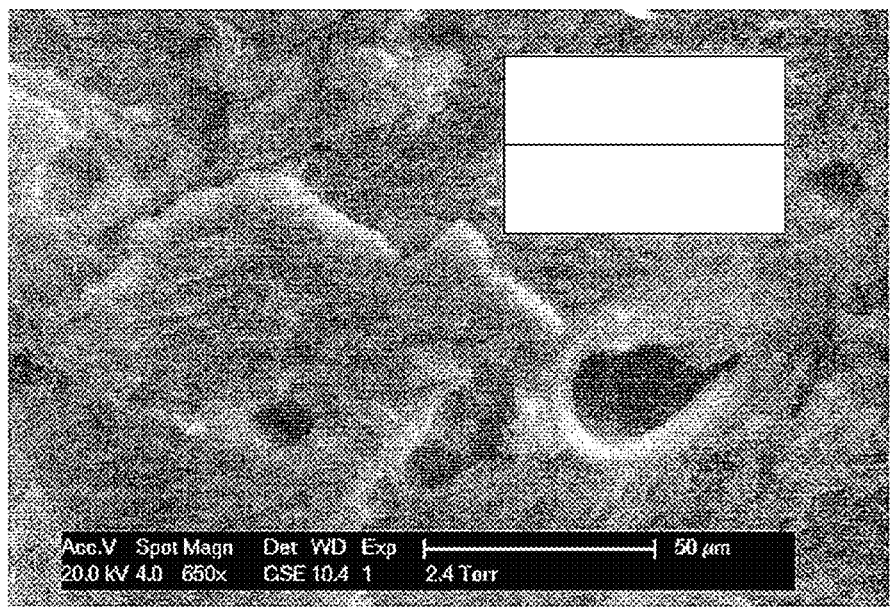
FIG. 7 gives a SEM image taken on a scale ranging from 0 to 50 μm of the bone regeneration material obtained using the method of the disclosure from bovine metaphysis.

FIGS. 5 to 7 are SEM images of the structure of the bone regeneration material obtained from bovine epiphysis (FIG. 5), calf metaphysis (FIG. 6) and bovine metaphysis (FIG. 7) respectively.

Among the different bone regeneration materials prepared according to Example 1, it is the material obtained from calf metaphysis which exhibits a macroporous structure similar to that of Bio-Oss®.

Example 2

100 g of degreased, defleshed bone material containing hydroxyapatite, 400 ml of demineralized water and 10 g NaOH were mixed in an autoclave reactor without agitator brought to a temperature of 230° C.±2° C. via external heating using an electric jacket. The pressure in the reactor was brought to 2500 kPa. These conditions of temperature and pressure were held for a time of two hours.

The reactor was cooled down to ambient temperature and depressurized to atmospheric pressure, a homogenous liquid phase was removed from the reactor by decanting so that only a solid phase remained in the reactor to which was added 3 g NaOH in solution in 400 ml of demineralized water.

The autoclave reactor was then brought to a temperature of 150° C. under atmospheric pressure (about 100 kPa) for a time of two hours.

The reactor was again cooled down to ambient temperature, the content of the reactor was decanted and the solid hydroxyapatite phase rinsed five times with demineralized water and then oven dried at a temperature of 120° C. until stabilization of its weight at around a stationary value.

The solid hydroxyapatite phase thus obtained was ground and screened in two fractions of 1.0-0.25 mm and 0.25-0.08 mm and then sterilized at 120° C. in airtight fluoropolymer bags for a time of 14 hours.

Example 3

100 g of degreased, defleshed bovine epiphysis containing hydroxyapatite, 400 ml of demineralized water and 15 g NaOH were mixed in an autoclave reactor without agitator brought to a temperature of 230° C.±2° C. via external heating using an electric jacket. The pressure in the reactor was brought to 2500 kPa. These conditions of temperature and pressure were held for a time of two hours.

The reactor was cooled down to ambient temperature and depressurized to atmospheric pressure, a first homogenous liquid phase was removed from the reactor by decanting so that only a solid phase remained in the reactor which was rinsed with demineralized water.

The solid phase was again mixed with 400 ml of demineralized water and 10 g NaOH and subjected a further time to the above-mentioned treatment.

A second homogenous liquid phase was removed from the reactor by decanting so that only a solid phase remained in the reactor to which was added 1 g NaOH in solution in 400 ml of demineralized water. The autoclave reactor was brought to a temperature of 150° C. under atmospheric pressure (about 100 kPa) for a time of two hours.

The reactor was again cooled down to ambient temperature, the content of the reactor decanted and the solid hydroxyapatite phase rinsed five times with demineralized water and then oven dried at a temperature of 120° C. until stabilization of its weight at around a stationary value.

The solid hydroxyapatite phase thus obtained was ground and screened in a single fraction at 1.0-0.25 mm.

Example 4

100 g of bone material were calcined in a muffle furnace at a temperature of 800° C.±2° C. for one hour until complete bleaching of the material.

After cooling, the solid hydroxyapatite phase thus obtained was ground and screened in two fractions of 1.0-0.25 mm and 0.25-0.08 mm, then sterilized at 120° C. in airtight fluoropolymer bags for a time of 14 hours.

Figure 8:
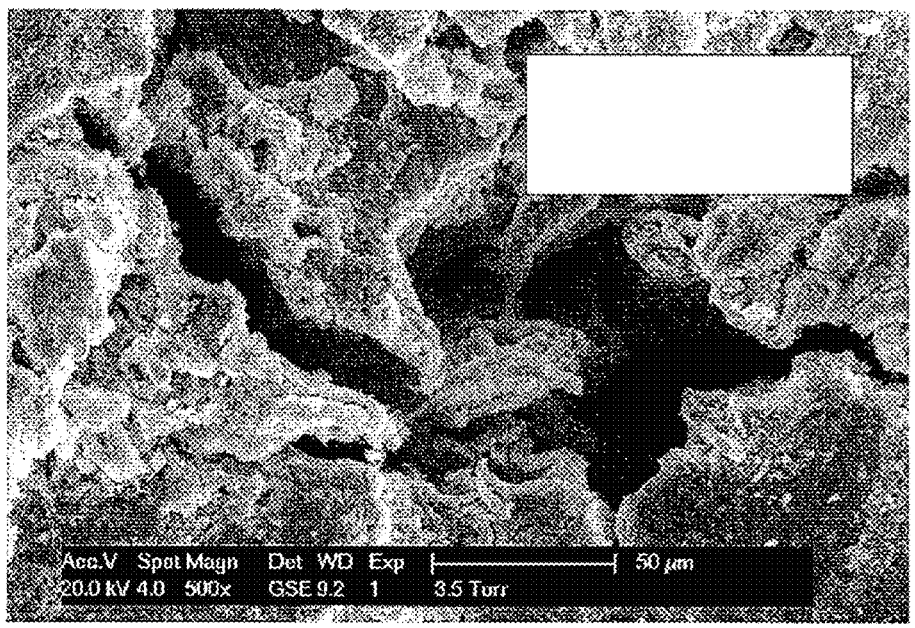
FIG. 8 gives two SEM images taken on a scale ranging from 0 to 100 μm of the bone regeneration material obtained from bovine epiphysis using a process whereby the bone material was calcined at 800° C.
Figure 8:
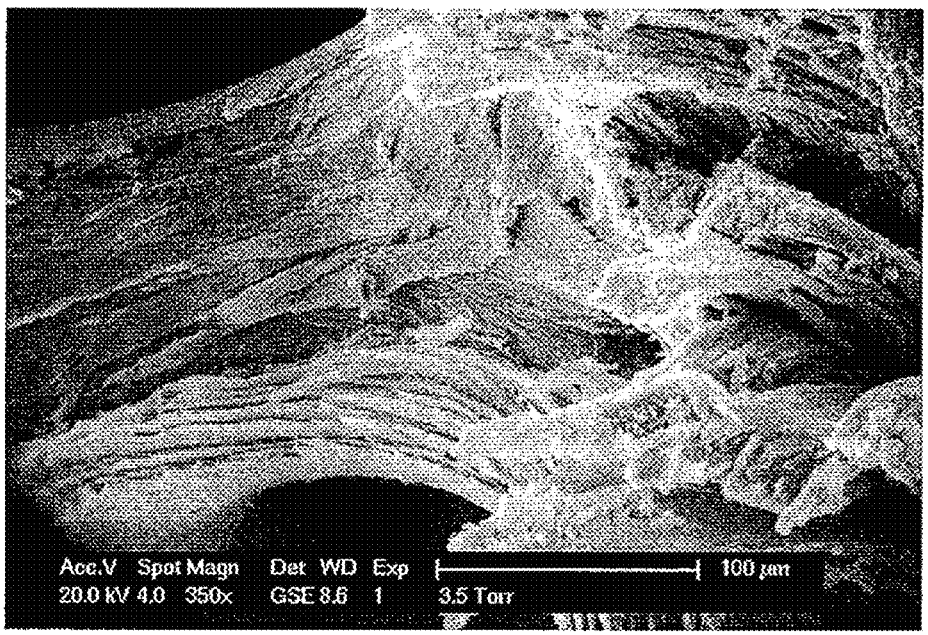

FIG. 8 illustrates the macroscopic structure under SEM imaging of the solid phase obtained following the protocol of Example 4. As shown in FIG. 8, calcining at 800° C. of the bone material produces a solid hydroxyapatite phase having a structure differing from that of Bio-Oss® since initiated collapse of the hydroxyapatite lattice can be seen resulting from reduced porosity of the structure, accompanied in addition by the onset of cracks of size in the order of 20 μm.

The results of this example tend to show that the treatment of hydroxyapatite at high temperature deteriorates the morphology and hence the osteoconductive properties of the bone regeneration material.

An increase in temperature up to 800° C. shows a reduction in the porous volumes of the hydroxyapatite structure, a reduction probably due to the onset of sintering.

Example 5

In the embodiment described in the present Example and contrary to the embodiments described in the preceding Examples, first cleaning of 1.7 Kg of calf epiphysis was carried out in two successive boiling steps for two hours in three liters of water in which 5 g NaOH were dissolved to form an aqueous basic solution that was renewed at each step.

After each boiling step the material was scraped to remove residues of flesh, marrow and cartilage.

The bone material thus treated was cut to a thickness of 5 mm. 100 g of this material, 400 ml of demineralized water and 10 g NaOH were mixed in an autoclave reactor without agitator brought to a temperature of 230° C.±2° C. via external heating using an electric jacket. The pressure in the reactor was brought to 2500 kPa. These conditions of temperature and pressure were held for a time of two hours.

The reactor was cooled down to a temperature of 50° C. and depressurized to atmospheric pressure, a homogeneous liquid phase was removed from the reactor by decanting so that only a solid phase remained in the reactor to which was added 3 g NaOH in solution in 400 ml of demineralized water. The autoclave reactor was then brought to a temperature of 150° C. under atmospheric pressure (about 100 kPa) for a time of two hours.

The reactor was again cooled down to ambient temperature, the content of the reactor decanted and the solid hydroxyapatite phase rinsed five times with demineralized water and then oven dried at a temperature of 120° C. until stabilization of its weight at around a stationary value.

The solid hydroxyapatite phase thus obtained was ground and screened in three fractions of 2.0-1.0 mm, 1.0-0.25 mm and less than 0.25 mm.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The invention claimed is:

1. A method to manufacture a bone regeneration material, comprising:
   contacting a bone material containing hydroxyapatite and organic substances with an extraction liquid giving rise to a first liquid phase containing said organic substances and optionally impurities extracted from said bone material, and to a second solid hydroxyapatite phase containing said hydroxyapatite; and
   separating said liquid phase from said solid hydroxyapatite phase,
   wherein said extraction liquid is an aqueous extraction solution brought to a temperature between 150° C. and 300° C. at a pressure of between 1500 kPa and 3500 kPa, and wherein said separated solid hydroxyapatite phase forms said bone regeneration material.

2. The method according to claim 1, further comprising an additional step of drying said solid hydroxyapatite phase to obtain a dry solid hydroxyapatite phase.

3. The method according to claim 2, wherein after said first separation step and before said drying step of said solid hydroxyapatite phase, the method comprises a second contacting step of said solid hydroxyapatite phase with a dilute aqueous solution of basic pH at a temperature between 150° C. and 300° C. and pressure of between 500 kPa and 1000 kPa, said dilute aqueous solution of basic pH containing a strong base at a concentration between 0.05 and 0.4 N, said second contacting step being followed by a second separation step between a second liquid phase and second solid phase which is then dried.

4. The method according to claim 3, wherein the strong base is at a concentration of between 0.1 and 0.3 N.

5. The method according to claim 2, wherein said solid hydroxyapatite phase is previously washed with water before being dried.

6. The method according to claim 2, wherein subsequent to said drying step, the method comprises a step of sterilizing said dry solid hydroxyapatite phase.

7. The method according to claim 1, wherein said aqueous extraction solution is water or a concentrated aqueous solution of basic pH comprising a strong base at a concentration of between 0.5 and 1 N.

8. The method according to claim 7, wherein the strong base is at a concentration of between 0.6 and 0.9 N.

9. The method according to claim 1, wherein prior to the first contacting step with said extraction liquid, the method comprises a step of degreasing and defleshing said bone material.

10. The method according to claim 1, wherein said bone material is of natural animal origin.

* * * * *